United States Patent
Bressler et al.

(10) Patent No.: US 7,018,344 B2
(45) Date of Patent: Mar. 28, 2006

(54) RETRACTABLE NEEDLE SHIELDING DEVICE

(75) Inventors: Peter Bressler, Philadelphia, PA (US); John Coleman, Philadelphia, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 323 days.

(21) Appl. No.: 10/347,960

(22) Filed: Jan. 21, 2003

(65) Prior Publication Data

US 2004/0143195 A1    Jul. 22, 2004

(51) Int. Cl.
*A61B 5/00* (2006.01)
*B65D 81/00* (2006.01)

(52) U.S. Cl. .................. 600/573; 604/198; 604/177
(58) Field of Classification Search ............... 600/573; 604/263, 171, 177, 198; 30/125
See application file for complete search history.

(56) References Cited

U.S. PATENT DOCUMENTS

| | | |
|---|---|---|
| 4,941,881 A | 7/1990 | Masters et al. |
| 5,067,946 A | 11/1991 | Zhadanov |
| 5,108,376 A | 4/1992 | Bonaldo |
| 5,167,635 A | 12/1992 | Haber et al. |
| 5,176,650 A | 1/1993 | Haining |
| 5,179,655 A | 1/1993 | Noguchi et al. |
| 5,219,339 A | 6/1993 | Saito |
| 5,330,438 A | 7/1994 | Gollobin et al. |
| 5,350,368 A | 9/1994 | Shields |
| 5,382,240 A | 1/1995 | Lam |
| 5,433,703 A | 7/1995 | Utterberg et al. |
| 5,501,672 A | 3/1996 | Firth et al. |
| 5,562,636 A | 10/1996 | Utterberg |
| 5,573,512 A | 11/1996 | Van den Haak |
| 5,704,917 A | 1/1998 | Utterberg |
| 5,746,215 A | 5/1998 | Manjarrez |
| 5,772,638 A | 6/1998 | Utterberg et al. |
| 5,800,400 A | 9/1998 | Hogan |
| 5,921,969 A | 7/1999 | Vallelunga et al. |
| 5,951,525 A | 9/1999 | Thorne et al. |
| 6,001,083 A | 12/1999 | Wilner |
| 6,210,371 B1 | 4/2001 | Shaw |

(Continued)

FOREIGN PATENT DOCUMENTS

EP    554 841 A1    8/1993

(Continued)

*Primary Examiner*—Max F. Hindenburg
*Assistant Examiner*—Brian Szmal
(74) *Attorney, Agent, or Firm*—Scott Rittman; Mark Schildkraut (57) ABSTRACT

The present invention is directed to a shieldable needle device. The shieldable needle device includes a hub having a lever extending from an external surface thereof, and a needle cannula with a puncture tip extending from said hub. The hub is interengaged with a housing having a main body portion with the needle cannula extending through a forward opening therein, and a rearward extension with a longitudinal slot extending axially therealong between a forward slot end and a rearward slot end, such that the lever of the hub extends through the longitudinal slot and is locked at the forward slot end thereof. The housing also includes a tip guard within the main body portion which is axially movable along the needle cannula. The lever is radially movable with respect to a longitudinal axis of the needle device to unlock the lever from the forward slot end, and is axially movable toward the rearward slot end to cause axial movement and to thereby retract the needle cannula, with the tip guard protectively covering the puncture tip of the needle cannula.

33 Claims, 6 Drawing Sheets

U.S. PATENT DOCUMENTS

| | | |
|---|---|---|
| 6,228,066 B1 | 5/2001 | Zhadanov et al. |
| 6,379,335 B1 | 4/2002 | Rigon et al. |
| 6,513,246 B1 * | 2/2003 | Ping .......................... 30/125 |
| 2001/0018573 A1 | 8/2001 | Woehr |

FOREIGN PATENT DOCUMENTS

| | | |
|---|---|---|
| EP | 1362608 A2 * | 11/2003 |
| WO | WO 00/02614 | 1/2000 |
| WO | WO 02/45786 | 6/2002 |

* cited by examiner

RETRACTABLE NEEDLE SHIELDING DEVICE

BACKGROUND OF THE INVENTION

1. Field of the Invention

The present invention relates to safety needle devices for safe and convenient handling of needles. More particularly, the present invention relates to a shieldable needle device having a forward moving safety shield for protection from a used needle tip.

2. Description of Related Art

Disposable medical devices having medical needles are used for administering medication or withdrawing fluid from the body of a patient. Such disposable medical devices typically include blood-collecting needles, fluid handling needles and assemblies thereof. Current medical practice requires that fluid containers and needle assemblies used in such devices be inexpensive and readily disposable. Consequently, existing blood collection devices typically employ some form of durable, reusable holder on which detachable and disposable medical needles and fluid collection tubes may be mounted. A blood collection device of this nature may be assembled prior to use and then disassembled after use. Thus, these blood collection devices allow repeated use of a relatively expensive holder upon replacement of relatively inexpensive medical needles and/or fluid collection tubes. In addition to reducing the cost of collecting blood specimens, these blood collection devices help minimize the production of hazardous waste material.

A blood collection device or intravenous (IV) infusion device typically includes a needle cannula having a proximal end, a pointed distal end, and a lumen extending therebetween. The proximal end of the needle cannula is securely mounted in a plastic hub defining a central passage that communicates with the lumen extending through the needle cannula. A thin, flexible thermoplastic tube is connected to the hub and communicates with the lumen of the needle cannula. The end of the plastic tube remote from the needle cannula may include a fixture for connecting the needle cannula to a blood collection tube or other receptacle. The specific construction of the fixture will depend upon the characteristics of the receptacle to which the fixture is to be connected.

In order to reduce the risk of incurring an accidental needle-stick wound, protection of used needle cannulas becomes important. With concern about infection and transmission of diseases, methods and devices to enclose or cover the used needle cannula have become very important and in great demand in the medical field. For example, needle assemblies commonly employ a safety shield that can be moved into shielding engagement with a used needle cannula to minimize risk of an accidental needle stick.

For example, U.S. Pat. No. 5,167,635 to Haber et al. discloses a safety IV catheter assembly including a catheter cannula which is retractable within a safety housing by rearward movement of a position control button through a slide track in the housing. The catheter cannula can be retained within the housing by positioning the control button within a locking detent at the rearward portion of the slide track. U.S. Pat. No. 5,501,672 to Firth et al. discloses hypodermic syringes and catheter devices in which a needle can be retracted within a wingset body. The body includes an open channel with pockets of varying widths, and the needle is connected to a slide member which slides within the channel. To retract the needle within the body, the slide member is depressed within the body, and tubing is pulled to retract the needle. U.S. Pat. No. 5,746,215 to Manjarrez discloses an IV device with an extendable and retractable needle. The needle can be extended against the force of a tension spring to lock in an extended state for use, and can be retracted by the tension spring to retract the needle within the housing. The device further includes a button which rides within a channel of the housing.

Such prior art devices are typically difficult to manufacture, require complex operation to operate, and do not provide for a needle clip for preventing re-emergence of the needle. In view of the foregoing, a need exists for a blood collection set including a shieldable needle device that achieves secure and effective shielding of a used needle cannula, which is easy to manufacture and is simple and safe to operate.

SUMMARY OF THE INVENTION

The present invention is directed to a shieldable needle device. The shieldable needle device includes a hub which has a lever extending from an external surface thereof. A needle cannula with a puncture tip extends from a forward end of the hub. The needle device further includes a housing having a main body portion with an internal opening and a forward opening accommodating the needle cannula extending therethrough, and a rearward extension having a longitudinal slot extending axially therealong between a forward slot end and a rearward slot end. The lever of the hub extends through the longitudinal slot and is locked at the forward slot end thereof, such as through a releasable locking mechanism which is in engagement with a portion of the rearward extension at the forward slot end of the longitudinal slot. The housing further includes a tip guard within the main body portion, which is axially movable with respect to the needle cannula. The lever is radially movable with respect to a longitudinal axis of the needle device to unlock it from the forward slot end, and is axially movable toward the rearward slot end. Such movement causes axial movement of the needle cannula through the forward opening of the housing, thereby retracting the needle cannula within the main body portion of the housing to a position with the tip guard protectively covering the puncture tip of the needle cannula. The housing may include a pair of generally planar wings to form a wingset housing, which is particularly adapted for connection to a blood collection set.

Desirably, the lever and the longitudinal slot are in frictional engagement along the longitudinal slot, thereby requiring a force to be exerted on the lever toward the rearward slot end to cause axial movement of the lever toward the rearward slot end. The lever may include a finger surface having a profile for accommodating a user's finger, such that the lever is axially movable toward the rearward slot end through pressure exerted on the finger surface. Also, the longitudinal slot is preferably free of a rearward locking mechanism, and is desirably of substantially uniform width between the forward slot end and the rearward slot end.

The tip guard may be a resiliently deflectable material, and desirably includes a deflectable one-piece clip-like member including a forward end and a rearward end with a spring leg extending therebetween mounted within the housing. For example, the forward end can be bent to form a lockout leg, and the rearward end may include a bend to form a rearward extent, with each of the rearward end and the rearward extent including openings for accommodating the needle cannula therethrough. As such, the spring leg is biased against the needle cannula during axial movement of the needle cannula and the lockout leg is resiliently moved over the puncture tip of the needle cannula when the needle cannula is retracted within the main body portion.

In a further embodiment, the needle device may include means for, storing energy such as a compression spring extending between the housing and the hub, wherein the stored energy is released upon radial movement of the lever, thereby forcing the hub away from the housing and causing axial movement of the lever along the longitudinal slot to retract the needle cannula within the housing to a position with the tip guard protectively covering the puncture tip of the needle cannula.

The present invention is also directed to a safety blood collection set including a needle device connected with a flexible tube and a fixture for interconnecting the blood collection set to a receptacle. The needle device includes a hub mounted to an end of the flexible tube, with the hub including a lever extending from an external surface of the hub. A needle cannula having a puncture tip and an internal lumen extends from the hub such that the internal lumen is in fluid communication with the flexible tube through the hub. The needle device further includes a wingset housing having a main body portion with a forward opening and a tip guard within the housing, and a rearward extension with a longitudinal slot extending axially therealong between a forward slot end and a rearward slot end. The needle cannula extends from the forward opening, and the lever of the hub extends through the longitudinal slot and is locked at the forward slot end. The safety blood collection set is operable such that radial movement of the lever unlocks the lever from the forward slot end of the longitudinal slot, and axial movement of the lever toward the rearward slot end of the longitudinal slot causes axial movement of the needle cannula through the internal opening of the wingset housing to retract the needle cannula to a position with the tip guard protectively covering the puncture tip.

DETAILED DESCRIPTION

Figure 1:
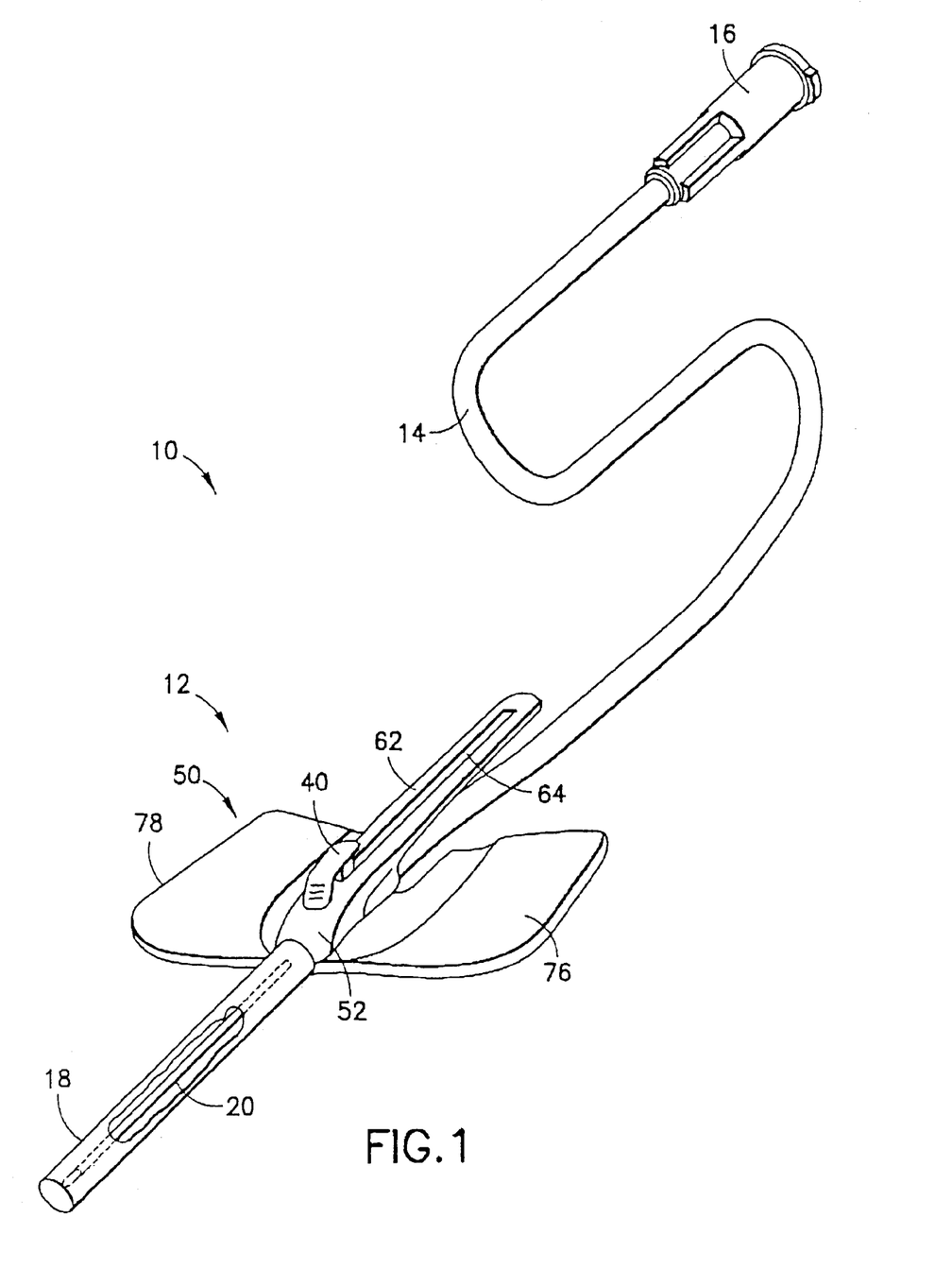
FIG. 1 is a perspective view of a blood collection set including a shieldable needle device, in accordance with the present invention, showing a partial cutaway of a packaging cover.

Referring to the drawings in which like reference characters refer to like parts throughout the several views thereof, FIG. 1 illustrates a blood collection set, including a shieldable needle device in accordance with the present invention and the related features. The present invention is generally described in terms of a shieldable needle device. FIG. 1 illustrates the shieldable needle device in the form of a blood collection set 10, including a shieldable needle device 12. While described herein in terms of one embodiment of a blood collection set, the shieldable needle device of the present invention may be used with or incorporate other medical devices used in connection with a needle, such as a hypodermic syringe assembly, a hypodermic needle, a double ended needle assembly for blood collection, an intravenous infusion set, or other handling devices or medical device assemblies that contain piercing elements.

As shown in FIG. 1, blood collection set 10 includes a shieldable needle device 12, a flexible tube 14 extending from needle device 12, a fixture 16 mounted to tube 14, and a packaging cover 18 removably mounted to portions of needle device 12 opposite tube 14, such as through frictional engagement. Shieldable needle device 12 of blood collection set 10 is shown in detail in FIGS. 2–7, and generally includes a needle cannula 20, a hub 30 including a lever 40, and a housing 50 including a main body portion 52 and a rearward extension 62.

Needle cannula 20 includes a proximal or rearward end 22 and a distal or forward end 24, with lumen 26 extending through needle cannula 20 from rearward end 22 to forward end 24. Forward end 24 of needle cannula 20 is beveled to define a sharp puncture tip 28, such as an intravenous puncture tip. Puncture tip 28 is provided for insertion into a patient's blood vessel, such as a vein, and is therefore designed to provide ease of insertion and minimal discomfort during venipuncture.

Needle device 12 further includes hub 30. Hub 30 includes a proximal or rearward end 32 and a distal or forward end 34, with internal opening 36 extending therebetween. Rearward end 22 of needle cannula 20 is attached to hub 30 such that needle cannula 20 extends from forward end 34 of hub 30, with lumen 26 and internal opening 36 in fluid communication. For example, rearward end 22 of needle cannula 20 may be adhesively affixed within internal opening 36 of hub 30. Hub 30 may further include rim 38 provided for connection with flexible tube 14. Alternately, hub 30 may include any type of connection means for connecting needle assembly 12 with any desirable medical device for a specific intended use. For example, flexible tube 14 may extend within internal opening 36 of hub 30, with rearward end 22 of needle cannula 20 attached directly to flexible tube 14. In such an embodiment, rearward end 32 of hub 30 may be directly attached around flexible tube 14, such as by frictional engagement, or through an adhesive or the like.

Hub 30 further includes lever 40 extending radially from an external surface of hub 30. Desirably, lever 40 is integrally formed with hub 30, including an extension arm 42 extending from an outer surface of hub 30 to finger surface 44. Finger surface 44 desirably includes a surface having a profile for accommodating a user's finger, such as ribs or bumps 46. Desirably, finger surface 44 of lever 40 includes a bend 47 which provides flexibility to finger surface 44, as will be discussed in further detail herein.

Needle device 12 further includes housing 50. Housing 50 is a unitary structure, desirably molded from a thermoplastic material. Housing 50 includes a main body portion 52 having a forward end 52 and a rearward end 56, with a generally open body defining internal opening 58. Forward end 52 includes a forward opening extending through the wall of main body portion 52 into internal opening 58.

Housing 50 further includes rearward extension 62 extending rearwardly from rearward end 56 of main body portion 52 generally along the direction of longitudinal axis 120. Rearward extension 62 includes a longitudinal slot 64 extending along the length thereof between forward slot end 66 and rearward slot end 68. Longitudinal slot 64 may further include an enlarged portion defined by forward slot edges 70 at forward slot end 66. Longitudinal slot 64 is further defined by side slot edges 72, 74 extending along the longitudinal length thereof. Desirably, side slot edges 72, 74 are substantially parallel and are of a substantially uniform width along the entire length of longitudinal slot 64, apart from the enlarged portion defined by forward slot edges 70 at forward slot end 66.

Housing 50 may further include a pair of stabilizers in the form of planar wings 76, 78 extending laterally from main body portion 53 at opposing sides thereof. Planar wings 76, 78 provide housing 50, and needle device 12, as a butterfly-type wingset assembly, assisting in positioning and placement of needle device and blood collection set 10 during blood collection procedures.

Figure 7:
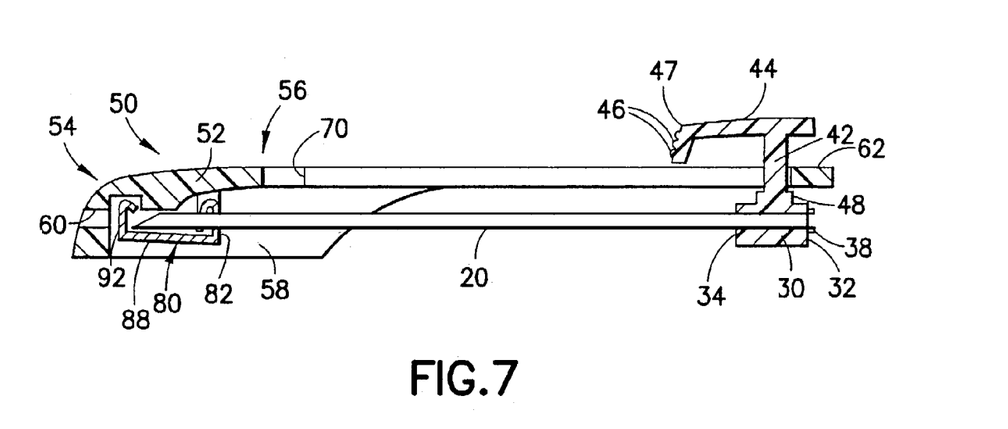
FIG. 7 is a cross-sectional view taken along line VII—VII of FIG. 6 with the needle device in a shielded state.
Figure 8:
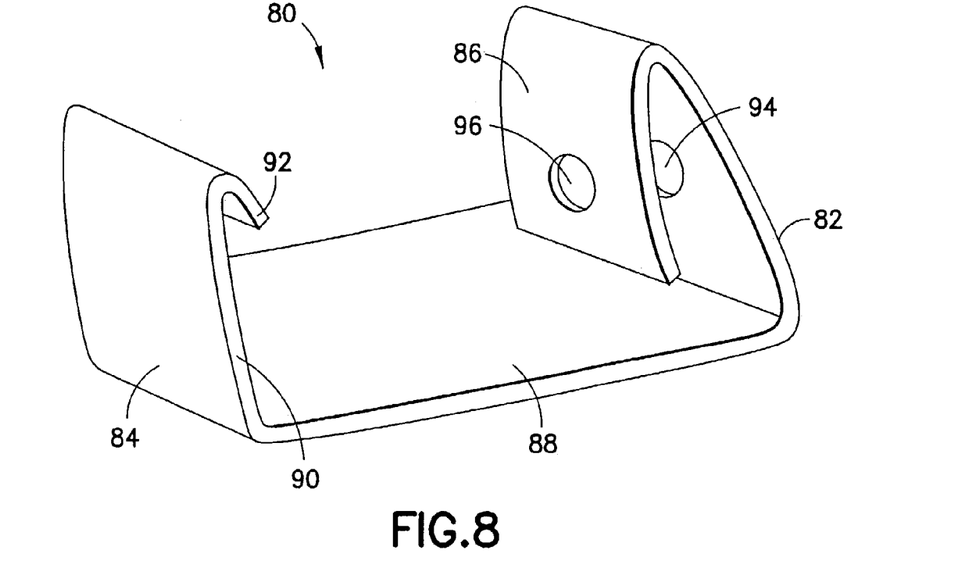
FIG. 8 is an enlarged perspective view of a tip guard as used with the present invention.

Needle device 12 further includes a locking assembly such as tip guard 80 positioned within internal opening 58 of main body portion 52 of housing 50. Tip guard 80 may be integrally formed with housing 50, or more desirably is a separate one piece clip-type member which is fixedly attached within internal opening 58. Tip guard 80 is desirably formed from a resiliently deflectable metallic material. As shown in more detail in FIG. 8, tip guard 80 generally includes rearward end 82 and forward end 84. Rearward end 82 is bent over itself at an upper portion thereof to form rearward extent 86. Rearward end 82 and forward end 84 are connected through bottom spring leg 88, which bends at forward end 84 to form front end wall 90. Front end wall 90 is further bent to form lockout leg 92. Internal opening 58 of main body portion 52 includes a profile to accommodate the shape of tip guard 80, with internal opening desirably having a pocket area for accommodating lockout leg 92, as depicted in FIG. 7. Rearward end 82 and rearward extent 86 include openings 94, 96, respectively, through the walls thereof, for accommodating needle cannula 20 therethrough, as will be discussed in more detail herein.

Lever 40 of hub 30 extends through longitudinal slot 64 of rearward extension 62. In particular, as shown in FIG. 4, extension arm 42 extends through longitudinal slot 64, with finger surface 44 extending from extension arm 42 beyond longitudinal slot 64 at the outer surface of housing 50.

Figure 2:
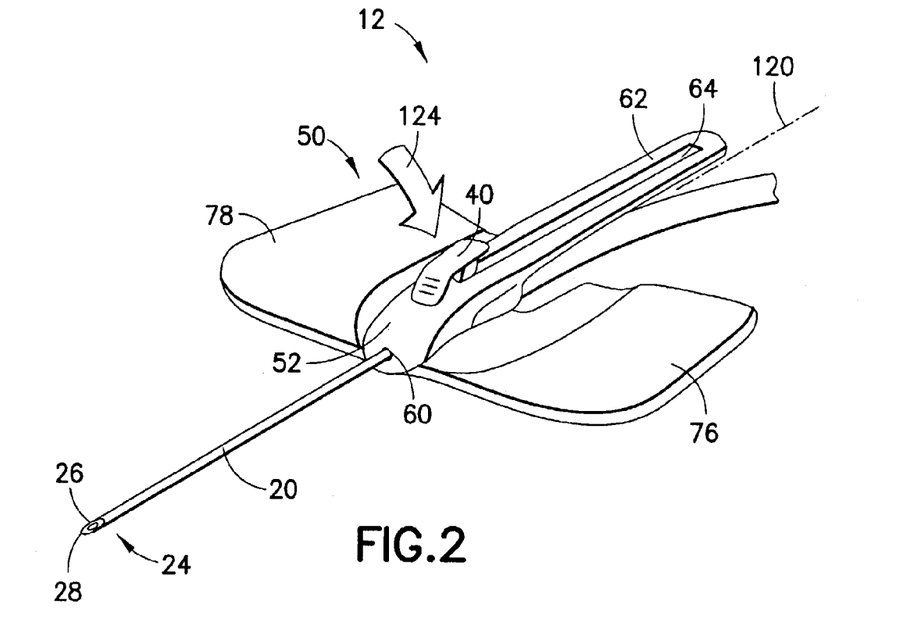
FIG. 2 is a perspective view of a shieldable needle device in accordance with the present invention shown in an extended or sampling state.
Figure 3:
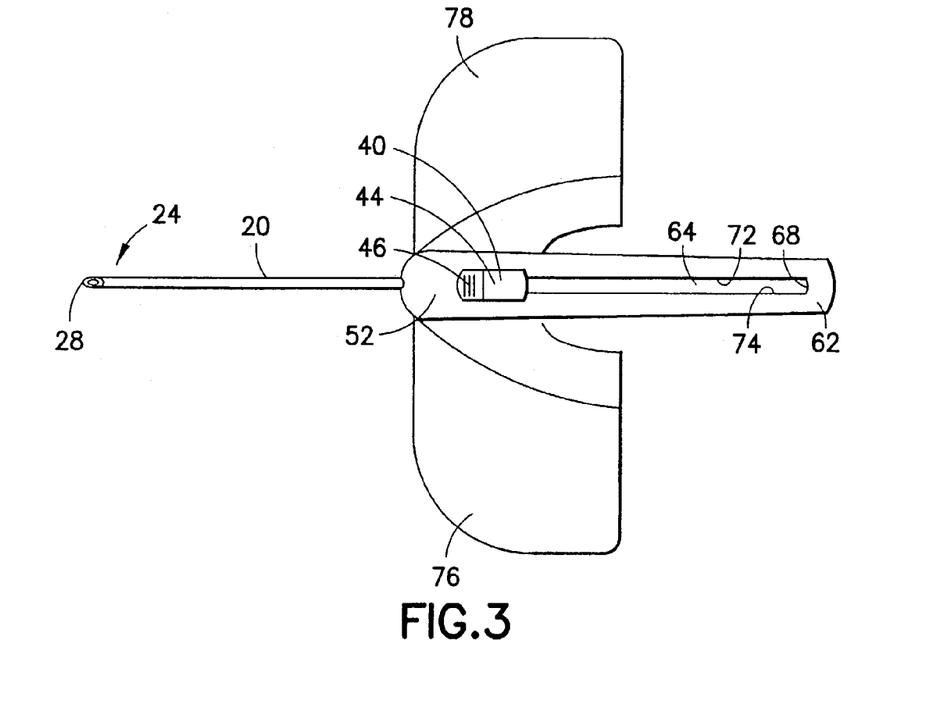
FIG. 3 is a top plan view of the needle device of FIG. 2.

Needle device 12 is capable of assuming a position for use and a position for protection from use. In particular, needle device 12 is operational in a first position as shown in FIGS. 2–4, in which needle cannula 20 extends within internal opening 58 and through forward opening 60 of main body portion 52 of housing 50. As such, needle device 12 is in a sampling state, with needle cannula 20 in an extended position extending from the forward end 56 of main body portion 52. Since needle cannula 20 is connected to hub 30, hub 30 is at a forward position with respect to housing 50, extending within internal opening 58 of main body portion 52. As such, lever 40 is at the forward slot end 66 of longitudinal slot 64 of rearward extension 62. To prevent needle cannula 20 from being released from the extended position, lever 40 is locked at the forward slot end 66. Such locking is accomplished through a locking mechanism such as enlarged portion 48 of extension arm 42 of lever 40, which is in an interference engagement with forward slot edges 70 of rearward extension 62 within the longitudinal slot 64, as shown in FIG. 4.

Figure 5:
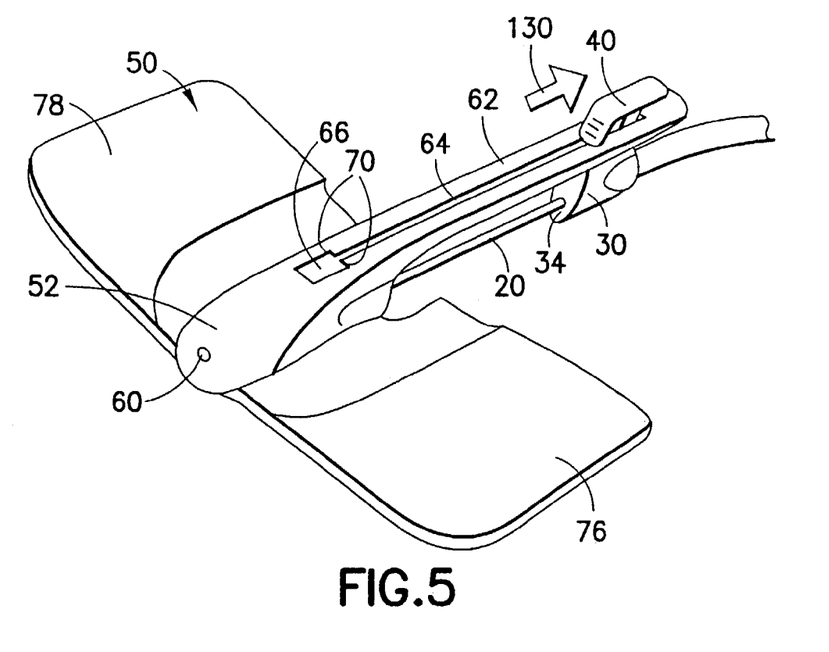
FIG. 5 is a perspective view of a shieldable needle device in accordance with the present invention shown in a fully retracted or shielded state.
Figure 6:
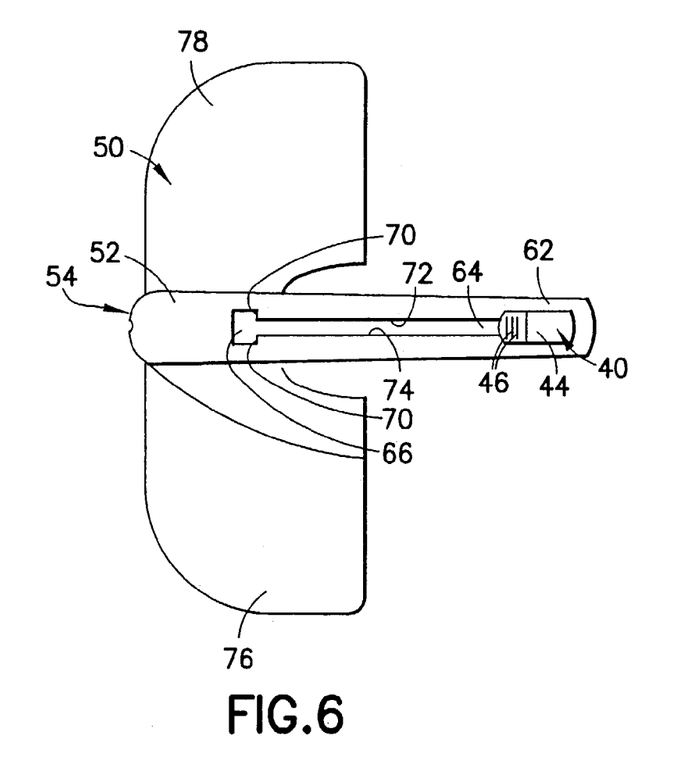
FIG. 6 is a top plan view of the needle device of FIG. 5.

Needle device 12 is also capable of assuming a position for protection from use, such as to provide for safety protection after the needle device has been used. In such a position, needle cannula 20 is in a retracted position with needle cannula retracted within internal opening 58 of main body portion 52 as shown in FIGS. 5–7. In such a position, hub 30 is in a rearward position with lever 40 at the rearward slot end 68 of longitudinal slot 64. Puncture tip 28 of needle cannula 20 is completely retracted within main body portion 52 of housing 50, with tip guard 80 protectively covering puncture tip 28 to prevent re-exposure thereof, as will be described in more detail.

Figure 4:
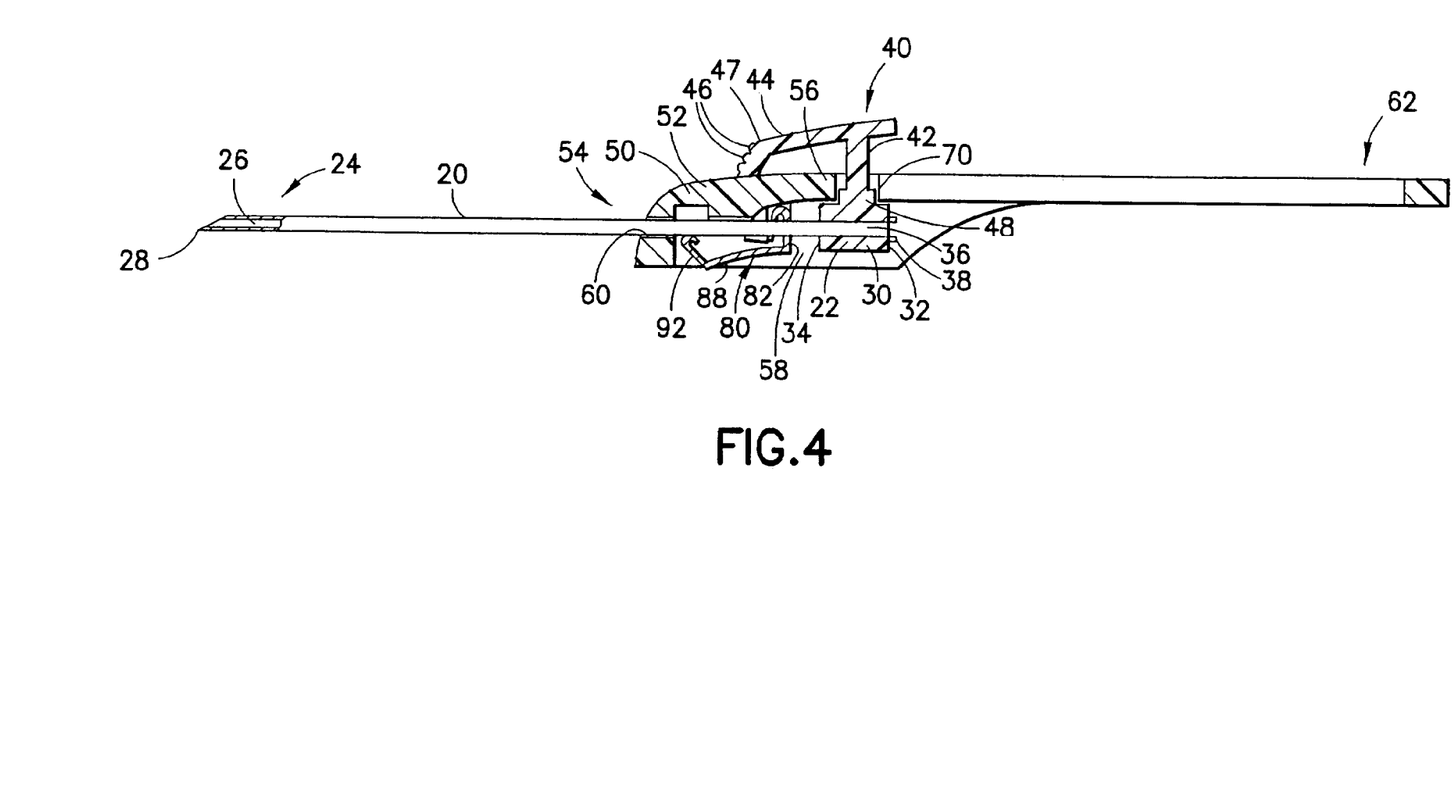
FIG. 4 is a cross-sectional view taken along line IV—IV of FIG. 3 with the needle device in an extended or sampling state.

Movement of needle cannula 20 between the extended position as shown in FIGS. 2–4 and the retracted position as shown in FIGS. 5–7 is accomplished through activation of lever 40, thereby actuating needle device 12 from the operation state to the protective safety shielded state. In particular, as noted above, in the operation state, needle cannula 20 extends from forward opening 60 of main body portion 50, with lever 40 locked in place such as through interference engagement between enlarged portion 48 and forward slot edges 70. In order to effect movement of needle cannula 20, lever 40 is activated by applying a radial force in a direction perpendicular to the longitudinal axis 120 of needle device 12, such as in the direction of arrow 124. Such radial force causes bend 47 of finger surface 44 to partially deflect due to the resilient nature of finger surface 44, which results in lever 40 and hub 30 also radially moving partially off-center of longitudinal axis 120. Such radial movement disengages enlarged portion 48 of extension arm 42 from interference engagement with forward slot edges 70 at longitudinal slot 64 of rearward extension 62. This releases lever 40 from the locked position, thus allowing free movement of lever 40 within longitudinal slot 64.

In order to effect retraction of needle cannula 20, lever 40 is moved axially along longitudinal axis 120 in a rearward direction toward rearward slot end 68 in the direction of arrow 130. This may be accomplished by exerting pressure on finger surface 44 of lever 40 in the direction of arrow 130. Bumps 46 provide an effective tactile surface for such finger pressure, while bend 47 provides finger surface 44 with a slight inclined angle surface to further assist in exerting a force in a rearward direction. Such finger pressure causes extension arm 42 of lever 40 to slide or guide through longitudinal slot 64, which causes hub 30 to move in a rearward direction. Since needle cannula 20 is connected to hub 30, needle cannula 20 is also moved in a rearward direction. As lever 40 is moved to rearward slot end 68, puncture tip 28 of needle cannula 20 retracts through forward opening 60 of main body portion 52. Since tip guard 80 is retained within internal opening 58 of main body portion 52, needle cannula 20 retracts and slides through openings 94 and 96 of tip guard 80, while bottom spring leg 88 is deflected such that lockout leg 92 slides along the outer surface of needle cannula 20 during such retraction. Once lever 40 is fully moved to rearward slot end 68, puncture tip 28 is retracted beyond forward opening 60 of main body portion 52 and beyond forward end 84 of tip guard 80, such that bottom spring leg 88 of tip guard 80 springs to its natural state, with lockout leg 92 assuming a position covering puncture tip 28 of needle cannula 20, thereby preventing movement of needle cannula 20 in a forward direction and thus preventing re-exposure of puncture tip 28 from housing 50.

By providing tip guard 80 within main body portion 52, needle cannula 20 is effectively locked within housing 50 without any further action required on the part of the user such as by engaging a locking mechanism between the lever 40 and the longitudinal slot 64. In this manner, longitudinal slot 64 is free of any rearward locking mechanism at rearward slot end 68, since needle cannula 20 is effectively locked in place through tip guard 80.

The length of longitudinal slot 64 should be sufficient to cause full retraction of needle cannula 20 within internal opening 58 of main body portion 52, and deflection of tip guard 80 over puncture tip 28, when lever 40 is at rearward slot end 68 of longitudinal slot 64, and preferably just prior to lever 40 being positioned at rearward slot end 68, to ensure full retraction of needle cannula 20.

Desirably, lever 40 and the walls of rearward extension 62 forming longitudinal slot 64 are in frictional engagement For example, the width of extension arm 42 desirably is approximately the same width as longitudinal slot 64, such that extension arm 42 frictionally engages side slot edges 72, 74. In this manner, lever 40 can be partially moved to a position along longitudinal slot 64 to partially retract needle cannula 20, for example after the needle cannula 20 has been inserted into a patient during a procedure. Also, with such a frictional engagement, movement of lever 40 through longitudinal slot 64 requires a force to be exerted on lever 40 toward rearward slot end 68 to cause axial movement of lever 40, and therefore to cause retraction of needle cannula 20 to the safety shielded position.

Figure 9:
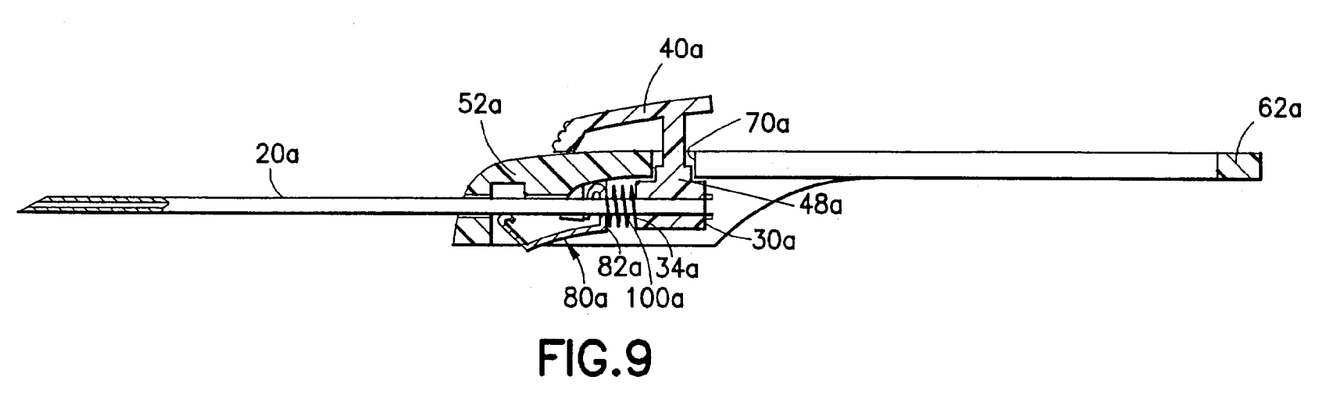
FIG. 9 is a side cross-sectional view of a needle device in an alternate embodiment of the present invention shown in an extended or sampling state.
Figure 10:
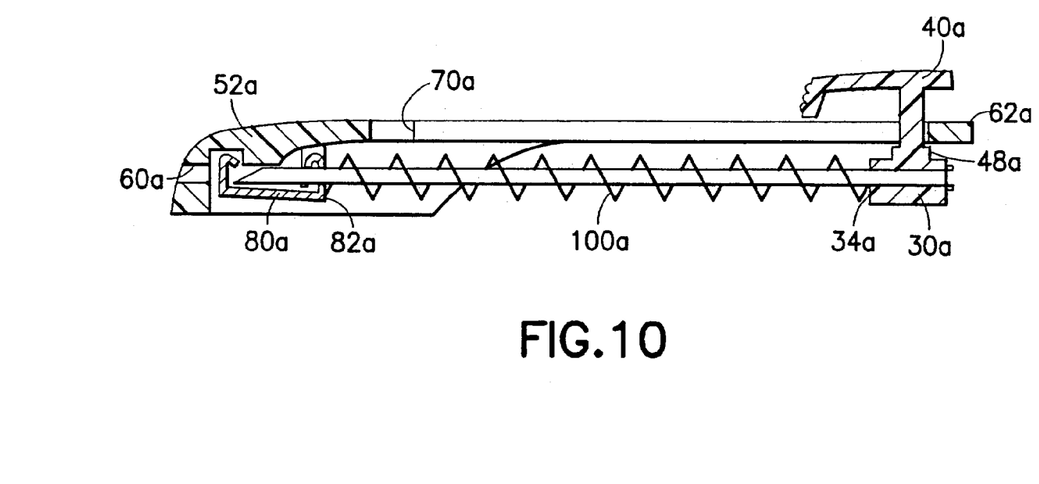
FIG. 10 is a side cross-sectional view of a needle device of the alternate embodiment shown in FIG. 9 in a retracted or shielded state.

Alternatively, as shown in FIGS. 9–10, needle device 12 may include means for storing energy extending between housing 50 and hub 30, such that upon release of the locking mechanism maintaining lever 40 at the forward slot end 66 of longitudinal slot 64, hub 30 is automatically forced rearwardly along longitudinal axis 120 in a direction of arrow 130, thereby automatically causing retraction and safety shielding of needle cannula 20. FIGS. 9–10 depict such a further embodiment of the present invention, and include many components which are substantially identical to the components of FIGS. 1–8. Accordingly, similar components performing similar functions will be numbered identically to those components of FIGS. 1–8, except that a suffix "a" will be used to identify those similar components in FIGS. 9 and 10.

The means for storing energy is shown generally in FIGS. 9–10 as a compression spring 100a. Compression spring 100a extends between rearward end 82a of tip guard 80a and forward end 34a of hub 30a. Compression spring 100a stores energy when in a compressed state, such as when needle device 12a is in an operational position with needle cannula 20a extending from forward opening 60a for a sampling procedure. When the locking mechanism maintaining lever 40a in place is released, the energy stored in compression spring 100a is released, thereby exerting a force in opposing directions between rearward end 82a of tip guard 80a and forward end 32a of hub 30a. As such, housing 50a and hub 30a are moved in opposing relative directions, thereby causing lever 40a to slide within longitudinal slot 64a in a rearward direction and causing retraction of needle cannula 20a.

The shieldable needle device of the present invention provides a unique structure for providing safety shielding of a needle tip for protection. The arrangement of the tip guard 80 within housing 50 provides for effective safety shielding of puncture tip 28. Moreover, the arrangement of lever 40 with finger surface 44 extending beyond longitudinal slot 64 allows for a simple mechanism for causing actuation of the shielding feature with a single hand of the user. In particular, by grasping main body portion 52 of housing 50 between the thumb and middle fingers, lever 40 can be effectively moved rearwardly by pressure of the index finger, thereby effectively retracting needle cannula 20 with a simple, one-handed mechanism. To further assist in such one-handed activation, it is contemplated that further structure can be added to the rearward portion of needle device 12, such as an extension of hub 30 or by coiling or bundling of flexible tube 14 for grasping with the palm of a user. Moreover, the arrangement of lever 40 and longitudinal slot 64 provides for an added safety feature for activation, in that activation of the shielding feature is achieved by moving the operating finger away from the needle tip while simultaneously moving the housing forward to the shielding position.

While the needle assembly of the present invention has been described in terms of an embodiment for use in connection with a blood collection system, it is further contemplated that the needle assembly could be used with other medical procedures, such as in conjunction with a conventional intravenous infusion set, a hypodermic needle assembly, or a double ended needle assembly for blood collection, all of which are well-known in the art for use with needle devices.

While the present invention is satisfied by embodiments in many different forms, there is shown in the drawings and described herein in detail, the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

What is claimed is:

1. A shieldable needle device comprising:
   a hub including a lever extending from an external surface thereof;
   a needle cannula extending from said hub, said needle cannula having a puncture tip; and
   a housing including a main body portion having a forward opening with said needle cannula extending through said main body portion from said forward opening, and a rearward extension having a longitudinal slot extending axially therealong between a forward slot end and a rearward slot end with said lever of said hub extending through said longitudinal slot and locked at said forward slot end thereof, said housing further including a tip guard within said main body portion;
   wherein said lever is radially movable with respect to a longitudinal axis of the needle device to unlock said lever from the forward slot end, and said lever is axially movable toward the rearward slot end causing axial movement of said needle cannula through said forward opening of said housing, thereby retracting said needle cannula within said main body portion of said housing to a position with said tip guard protectively covering said puncture tip of said needle cannula.

2. A shieldable needle device as in claim 1, wherein said lever and said longitudinal slot are in frictional engagement along said longitudinal slot, thereby requiring a force to be exerted on said lever toward said rearward slot end to cause axial movement of said lever toward said rearward slot end.

3. A shieldable needle device as in claim 1, wherein said lever includes a finger surface having a profile for accommodating a user's finger.

4. A shieldable needle device as in claim 3, wherein said lever is axially movable toward said rearward slot end through pressure exerted on said finger surface.

5. A shieldable needle device as in claim 1, wherein said tip guard includes a portion for accommodating said needle cannula during axial movement of said needle cannula for retraction within said main body portion.

6. A shieldable needle device as in claim 1, wherein said tip guard comprises a resiliently deflectable material.

7. A shieldable needle device as in claim 6, wherein said resiliently deflectable material includes a forward end and a rearward end with a spring leg extending therebetween, said forward end including a bend to form a lockout leg, said rearward end including a bend forming a rearward extent, each of said rearward end and said rearward extent including openings for accommodating said needle cannula therethrough, wherein said spring leg is biased against said needle cannula during axial movement of said needle cannula and said lockout leg is resiliently moved over said puncture tip of said needle cannula when said needle cannula is retracted within said main body portion.

8. A shieldable needle device as in claim 1, wherein said longitudinal slot is free of a rearward locking mechanism.

9. A shieldable needle device as in claim 1, wherein said longitudinal slot is of substantially uniform width between said forward slot end and said rearward slot end.

10. A shieldable needle device as in claim 1, further comprising means for storing energy extending between said housing and said hub, wherein the stored energy is released upon radial movement of said lever, thereby forcing said hub away from said housing and causing axial movement of said lever along said longitudinal slot to retract said needle cannula within said main body portion of said housing to a position with said tip guard protectively covering said puncture tip of said needle cannula.

11. A shieldable needle device as in claim 10, wherein said means for storing energy comprises a compression spring.

12. A shieldable needle device as in claim 1, wherein said lever includes a releasable locking mechanism for engagement with a portion of said rearward extension at said forward slot end to releasably lock said lever at said forward slot end of said longitudinal slot.

13. A shieldable needle device as in claim 12, wherein said lever comprises an extension arm with a finger surface extending beyond said longitudinal slot, and said locking mechanism comprises an enlarged portion of said extension arm for interference engagement with a wall of said longitudinal slot.

14. A shieldable needle device as in claim 1, wherein said housing includes a pair of generally planar wings extending from opposing sides of said housing.

15. A shieldable needle device as in claim 1, wherein said housing is adapted for connection to a blood collection set.

16. A shieldable needle device as in claim 1, including a packaging cover extending over said needle cannula.

17. A shieldable needle device comprising:
 a housing including a main body portion and a rearward extension extending from said main body portion, said main body portion including an internal opening extending therethrough with a locking assembly within said internal opening, said rearward extension including a longitudinal slot extending between a forward slot end adjacent said main body portion and a rearward slot end;
 a hub including a forward end, a rearward end, and an internal opening extending therethrough, said hub including a lever extending through said longitudinal slot of said housing, said lever including a finger surface extending beyond said longitudinal slot and a locking mechanism for locking said lever at said forward end of said longitudinal slot; and
 a needle cannula having a forward end extending from said forward end of said hub and into said internal opening of said main body portion of said housing;
 said lever being radially movable with respect to said longitudinal slot to release said locking mechanism of said lever from a locked position at said forward end of said longitudinal slot, said lever further being axially slidable along said longitudinal slot through said finger surface, thereby causing said needle cannula and said main body portion of said housing to axially move with respect to each other between an extended position in which said forward end of said needle cannula extends from a forward end of said main body portion of said housing and a retracted position in which said forward end of said needle cannula is retracted within said internal opening of said main body portion and said locking assembly engages said forward end of said needle cannula to prevent movement of said needle cannula from said retracted position to said extended position.

18. A shieldable needle device as in claim 17, wherein said lever and said longitudinal slot are in frictional engagement along said longitudinal slot, thereby requiring a force to be exerted on said lever toward said rearward slot end to cause axial movement of said lever toward said rearward slot end.

19. A shieldable needle device as in claim 17, wherein said lever comprises an extension arm extending between said hub and said finger surface, and said locking mechanism comprises an enlarged portion of said extension arm for interference engagement with a wall of said longitudinal slot.

20. A shieldable needle device as in claim 17, wherein said housing includes a pair of generally planar wings extending from opposing sides of said housing.

21. A shieldable needle device as in claim 17, wherein said locking assembly comprises a tip guard comprising a resiliently deflectable material.

22. A shieldable needle device as in claim 21, wherein said resiliently deflectable material includes a forward end and a rearward end with a spring leg extending therebetween, said forward end including a bend to form a lockout leg, said rearward end including a bend forming a rearward extent, each of said rearward end and said rearward extent including openings for accommodating said needle cannula therethrough, wherein said spring leg is biased against said needle cannula in said extended position and said lockout leg is resiliently moved over said puncture tip of said needle cannula in said retracted position.

23. A shieldable needle device as in claim 17, wherein said longitudinal slot is free of a rearward locking mechanism.

24. A shieldable needle device as in claim 17, wherein said longitudinal slot is of substantially uniform width between said forward slot end and said rearward slot end.

25. A safety blood collection set comprising:
 a fixture for connecting the blood collection set to a receptacle;

a flexible tube having opposed first and second ends, said first end of said flexible tube being connected to said fixture;

a hub mounted to said second end of said flexible tube, said hub including a lever extending from an external surface of said hub;

a needle cannula extending from said hub, said needle cannula having a puncture tip and an internal lumen in fluid communication with said flexible tube through said hub; and a wingset housing including a main body portion having a forward opening with said needle cannula extending from said forward opening, and a rearward extension having a longitudinal slot extending axially therealong between a forward slot end and a rearward slot end with said lever of said hub extending through said longitudinal slot and locked at said forward slot end, said wingset housing further including a tip guard within said main body portion;

wherein radial movement of said lever unlocks said lever from the forward slot end of said longitudinal slot, and axial movement of said lever toward the rearward slot end of said longitudinal slot causes axial movement of said needle cannula through said internal opening of said wingset housing, thereby retracting said needle cannula within said wingset housing to a position with said tip guard protectively covering said puncture tip of said needle cannula.

26. A safety blood collection set as in claim 25, wherein said lever and said longitudinal slot are in frictional engagement along said longitudinal slot, thereby requiring a force to be exerted on said lever toward said rearward slot end to cause axial movement of said lever toward said rearward slot end.

27. A safety blood collection set as in claim 25, wherein said lever includes a finger surface having a profile for accommodating a user's finger, and said lever is axially movable toward said rearward slot end through pressure exerted on said finger surface.

28. A safety blood collection set as in claim 25, further comprising a compression spring extending between said wingset housing and said hub, wherein radial movement of said lever causes energy stored in said compression spring to be released, thereby forcing said hub away from said wingset housing and causing axial movement of said lever along said longitudinal slot to retract said needle cannula within said main body portion of said wingset housing to a position with said tip guard protectively covering said puncture tip of said needle cannula.

29. A safety blood collection set as in claim 25, wherein said lever includes a releasable locking mechanism for engagement with a portion of said rearward extension at said forward slot end to releasably lock said lever at said forward slot end of said longitudinal slot.

30. A safety blood collection set as in claim 25, wherein said longitudinal slot is free of a rearward locking mechanism at said rearward slot end.

31. A safety blood collection set as in claim 25, wherein said longitudinal slot is of substantially uniform width between said forward slot end and said rearward slot end.

32. A safety blood collection set as in claim 25, wherein said tip guard comprises a resiliently deflectable material.

33. A safety blood collection set as in claim 32, wherein said resiliently deflectable material includes a forward end and a rearward end with a spring leg extending therebetween, said forward end including a bend to form a lockout leg, said rearward end including a bend forming a rearward extent, each of said rearward end and said rearward extent including openings for accommodating said needle cannula therethrough, wherein said spring leg is biased against said needle cannula during axial movement of said needle cannula and said lockout leg is resiliently moved over said puncture tip of said needle cannula when said needle cannula is retracted within said main body portion.

* * * * *